(12) United States Patent
Burgmann

(10) Patent No.: US 10,492,269 B2
(45) Date of Patent: Nov. 26, 2019

(54) PHOTOARRAY SYSTEM ILLUMINATION PATTERNS AND POWER MANAGEMENT

(71) Applicant: Stronach Medical Group, Inc., Aurora (CA)

(72) Inventor: Thomas A. D. Burgmann, Mississauga (CA)

(73) Assignee: Innova Technology Inc., Mississauga (CA)

( * ) Notice: Subject to any disclaimer, the term of this patent is extended or adjusted under 35 U.S.C. 154(b) by 8 days.

(21) Appl. No.: 15/114,676

(22) PCT Filed: Jan. 27, 2015

(86) PCT No.: PCT/CA2015/000054
§ 371 (c)(1),
(2) Date: Jul. 27, 2016

(87) PCT Pub. No.: WO2015/109395
PCT Pub. Date: Jul. 30, 2015

(65) Prior Publication Data
US 2018/0177020 A1 Jun. 21, 2018

Related U.S. Application Data

(60) Provisional application No. 61/931,771, filed on Jan. 27, 2014.

(51) Int. Cl.
*A61N 2/00* (2006.01)
*H05B 37/02* (2006.01)
(Continued)

(52) U.S. Cl.
CPC .............. *H05B 37/02* (2013.01); *A61N 5/06* (2013.01); *A61N 5/0621* (2013.01);
(Continued)

(58) Field of Classification Search
CPC ........................................................................
A61B 2017/00057; A61B 2017/00061;
A61B 2017/00066; A61N 5/06;
(Continued)

(56) References Cited

U.S. PATENT DOCUMENTS 7,476,888 B2 * 1/2009 Fiset .................... A61N 5/0614
250/365
7,592,276 B2 9/2009 Hill et al.
(Continued)

FOREIGN PATENT DOCUMENTS

WO  WO2010093753  8/2010

*Primary Examiner* — Thuy V Tran
(74) *Attorney, Agent, or Firm* — Ridout & Maybee LLP

(57) ABSTRACT

Embodiments of a photoarray system are provided. In one embodiment, a photoarray system includes a lixel array comprising a plurality of lixels each supporting one or more radiation sources; a power source associated with the lixel array; and a control system associated with the power source and each of the radiation sources, the control system comprising a master processor-readable medium configured to store at least a portion of data that specifies at least one lixel illumination pattern, the control system further comprising master processing structure configured to regulate use of power individually by each of the radiation sources based on the at least one lixel illumination pattern.

18 Claims, 7 Drawing Sheets

(51) Int. Cl.
*H05K 7/20* (2006.01)
*A61N 5/06* (2006.01)
*F21V 23/00* (2015.01)
*G01K 13/00* (2006.01)
*A61B 17/00* (2006.01)
*H02G 3/03* (2006.01)
*H02G 3/30* (2006.01)
*A61B 18/00* (2006.01)

(52) U.S. Cl.
CPC .......... *A61N 5/0624* (2013.01); *F21V 23/003* (2013.01); *G01K 13/00* (2013.01); *H05K 7/20509* (2013.01); *A61B 2017/00057* (2013.01); *A61B 2017/00061* (2013.01); *A61B 2017/00075* (2013.01); *A61B 2018/00642* (2013.01); *A61B 2018/00797* (2013.01); *A61N 2005/0626* (2013.01); *A61N 2005/0629* (2013.01); *A61N 2005/0645* (2013.01); *A61N 2005/0652* (2013.01); *A61N 2005/0658* (2013.01); *A61N 2005/0659* (2013.01); *A61N 2005/0662* (2013.01); *H02G 3/03* (2013.01); *H02G 3/30* (2013.01)

(58) Field of Classification Search
CPC .... A61N 2005/0628; A61N 2005/0629; A61N 2005/0651; A61N 2005/0652; A61N 2005/0658; A61N 2005/0659; A61N 2005/0661; A61N 2005/0662
See application file for complete search history.

(56) References Cited

U.S. PATENT DOCUMENTS

| | | | |
|---|---|---|---|
| 8,329,493 | B2 | 12/2012 | Mascaro et al. |
| 9,005,101 | B1* | 4/2015 | Van Erlach ...... A61B 17/22004 600/9 |
| 9,227,082 | B2* | 1/2016 | McDaniel ............ A61B 18/203 |
| 2007/0129776 | A1 | 6/2007 | Robins et al. |
| 2007/0208395 | A1* | 9/2007 | Leclerc ................ A61N 5/0616 607/86 |
| 2011/0301673 | A1 | 12/2011 | Hoffer et al. |
| 2012/0201024 | A1 | 8/2012 | van de Ven |
| 2012/0327048 | A1 | 12/2012 | Ramrattan et al. |
| 2013/0030264 | A1* | 1/2013 | Gopalakrishnan ... A61N 5/0621 600/310 |

* cited by examiner

PHOTOARRAY SYSTEM ILLUMINATION PATTERNS AND POWER MANAGEMENT

CROSS-REFERENCE TO RELATED APPLICATION

This application is a U.S. national stage entry under 35 U.S.C. 371 of PCT patent application PCT/CA2015/000054, filed Jul. 27, 2016, which designates the United States and was published in English. This application claims priority to U.S. Provisional Patent Application Ser. No. 61/931,771 filed on Jan. 27, 2014, the contents of which are incorporated entirely herein by reference.

FIELD OF THE INVENTION

The following relates generally to photoarray systems, and more particularly to photoarray system illumination patterns and power management.

BACKGROUND OF THE INVENTION

Light therapy involves administering doses of optical radiation to the body of a recipient of the therapy. Various light therapy systems are known, including those having one or more radiation sources incorporated into a housing that is designed to be held and aimed by a therapist to direct optical radiation towards a patient during a therapy session. Other light therapy systems include a flexible substrate with which is integrated an array of radiation sources. Such flexible photoarray systems are designed to conform to a non-planar portion of the recipient's body thereby to enable the radiation sources to be proximate to a region of interest, such as against the recipient's skin, without having to be constantly held in position by the therapist for the duration of a treatment session.

A flexible photoarray system is generally intended to be positioned directly proximate to the body of the recipient of the optical radiation. With such a configuration, the therapist is not generally able to observe the skin or other body surface of the recipient where it is occluded by the flexible photoarray system. Furthermore, a recipient of the light therapy, typically unfamiliar with the therapy process, may not raise concerns about discomfort or may not even feel discomfort despite heat levels in various areas between the flexible photoarray system and the recipient's body with which it is directly proximate being higher than is healthy for the recipient. Similarly, the therapist and recipient are not typically able to visually gauge whether an effective amount of radiation has been administered to the region of interest.

In addition, it would be useful for a flexible photoarray system to be portable to the extent that it could remain on the recipient, unsupervised by a therapist, for extended periods while the recipient is doing some other activity. However, facilitating portability and unsupervised use raises unique challenges in how each of power management, heat management, treatment duration and dose monitoring and the like are addressed.

SUMMARY OF THE INVENTION

According to an aspect, there is provided a photoarray system comprising a lixel array comprising a plurality of lixels each supporting one or more radiation sources; a power source associated with the lixel array; and a control system associated with the power source and each of the radiation sources, the control system comprising a master processor-readable medium configured to store at least a portion of data that specifies at least one lixel illumination pattern, the control system further comprising master processing structure configured to regulate use of power individually by each of the radiation sources based on the at least one lixel illumination pattern.

According to another aspect, there is provided a photoarray system comprising a lixel array comprising a plurality of lixels, each lixel comprising at least two radiation sources; and a control system having a power supply, the control system configured to individually control each radiation source to emit radiation and to cause different voltages to be provided to the lixels based on which of the at least two radiation sources is to be actuated.

Other aspects and advantages will become apparent from the following description.

BRIEF DESCRIPTION OF THE DRAWINGS

Embodiments will now be described with reference to the appended drawings in which.

DETAILED DESCRIPTION

The following description relates to photoarray systems, and description is provided of a photoarray system comprising a granularly controllable lixel array having a plurality of lixels each having one or more radiation sources. The lixel array of the photoarray system preferably delivers high power optical energy from the radiation sources in close proximity over a large epidermal surface area on human or animal patients. Providing individual control over each of the plurality of radiation sources facilitates maintaining thermal energy at comfortable levels for a patient, while facilitating efficient delivery of electrically-powered radiation.

In this description, the term "lixel" refers to an electronic module comprising one or more radiation sources for emitting non-ionizing radiation such as visible, infrared and/or ultraviolet light and that is individually controllable to cause its one or more radiation sources to be actuated.

Figure 1:
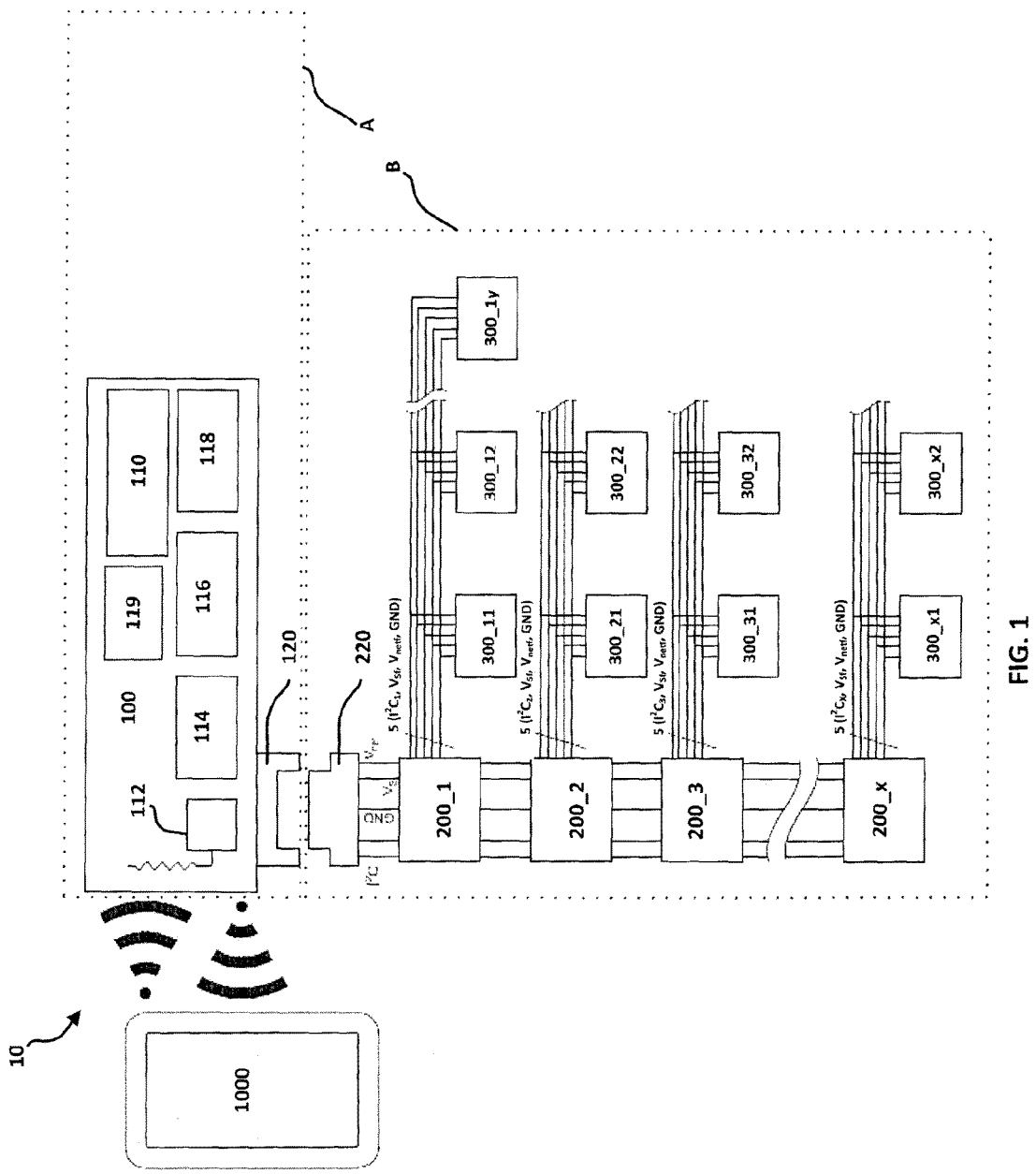
FIG. 1 is a schematic diagram of a photoarray system according to an embodiment.

Turning to FIG. 1, there is shown a schematic diagram of a photoarray system 10 according to an embodiment. Photoarray system 10 includes a control system A in power and data communications with a lixel array B.

In this embodiment, control system A includes a main control module 100 having a master microcontroller 110 as its processing structure along with processor-readable memory, and a radiofrequency transceiver 112 configured to provide wireless data communications with an external computing device 1000 such as a desktop computer, a laptop computer, a Smartphone or a tablet having a similar transceiver and equipped to operate according to standard communications protocols. Such protocols may include WIFI, Bluetooth™, Bluetooth low-energy, ZigBee, ANT, ANT+, MICS, MBAN, MDDS, WMTS, Wireless USB, Z-Wave, 3G, and 4G (LTE) and other hardware/software protocols which may become adopted for short to medium range wireless communications. For example, main control module 100 may be programmed or re-programmed with instructions provided via RF transceiver 112.

Main control module 100 also includes a power section 114, a human/machine interface 116, and a rechargeable battery 118. In this embodiment, human/machine interface 116 includes touch-sensitive controls for actuation and other functions, the operation of which is well known and will not be described further herein.

Main control module 100 also includes a first power/data interface 120 that can be mated with a second power/data interface 220 with which a plurality of communication link modules, or "commlinks" 200 (which are numbered individually as 200_1, 200_2, 200_3 to 200_x in FIG. 1) of control system A are in power and data communications. In this description, a commlink 200 is an electronic module that is electrically linked to both the main control module 100 and a respective lixel or lixels 300 as will be described, and serves an intermediate control function under the control of, and in cooperation with, the main control module 100, as will be described.

In this embodiment, main control module 100 provides power through power/data interface 120 along three (3) electrical lines, namely a fixed voltage line $V_s$ (which would typically be fixed at 5 VDC or 3.3 VDC though other fixed voltages can be used), a variable voltage line $V_{net}$, and a ground (GND) line. Furthermore, in this embodiment, main control module provides data communications along two (2) lines forming an I²C (Inter-Integrated Circuit) serial data bus, namely a serial clock line (I²C SCL) and a serial data line (I²C SDA).

In this embodiment, lixel array B includes a plurality of lixels 300, each of which are in power and data communications via the three (3) power lines and the two (2) data lines with a respective commlink 200. In particular, each commlink 200_1 . . . 200_x is in power and data communications with a respective subset of the plurality of lixels 300. As shown in FIG. 1, commlink 200_1 is in power and data communications with each of lixels 300_11, 300_12, . . . 300_1y, where y is an integer number representing the number of lixels in power and data communications with commlink 200_1. Similarly, commlink 200_2 is in power and data communications with each of lixels 300_21, 300_22 and so forth, and commlink 200_3 is in power and data communications with each of lixels 300_31, 300_32 and so forth. The photoarray system 10 may be configured to have up to x commlinks 200, each of which (when first and second interfaces 120 and 220 are connected) is in power and data communications with both the main control module 100 and a respective subset of the lixels 300. As such, commlink 200_x is in power and data communications with each of lixels 300_x1, 300_x2 and so forth.

The number of lixels 300 that are in power and data communications with a respective commlink 200 is not fixed, and may not be the same across all commlinks 200_1 to 200_x. Accordingly, for example, commlink 200_1 may be in power and data communications with one number of lixels 300, and commlink 200_2 may be in power and data communications with a different number of lixels 300.

Figure 2:
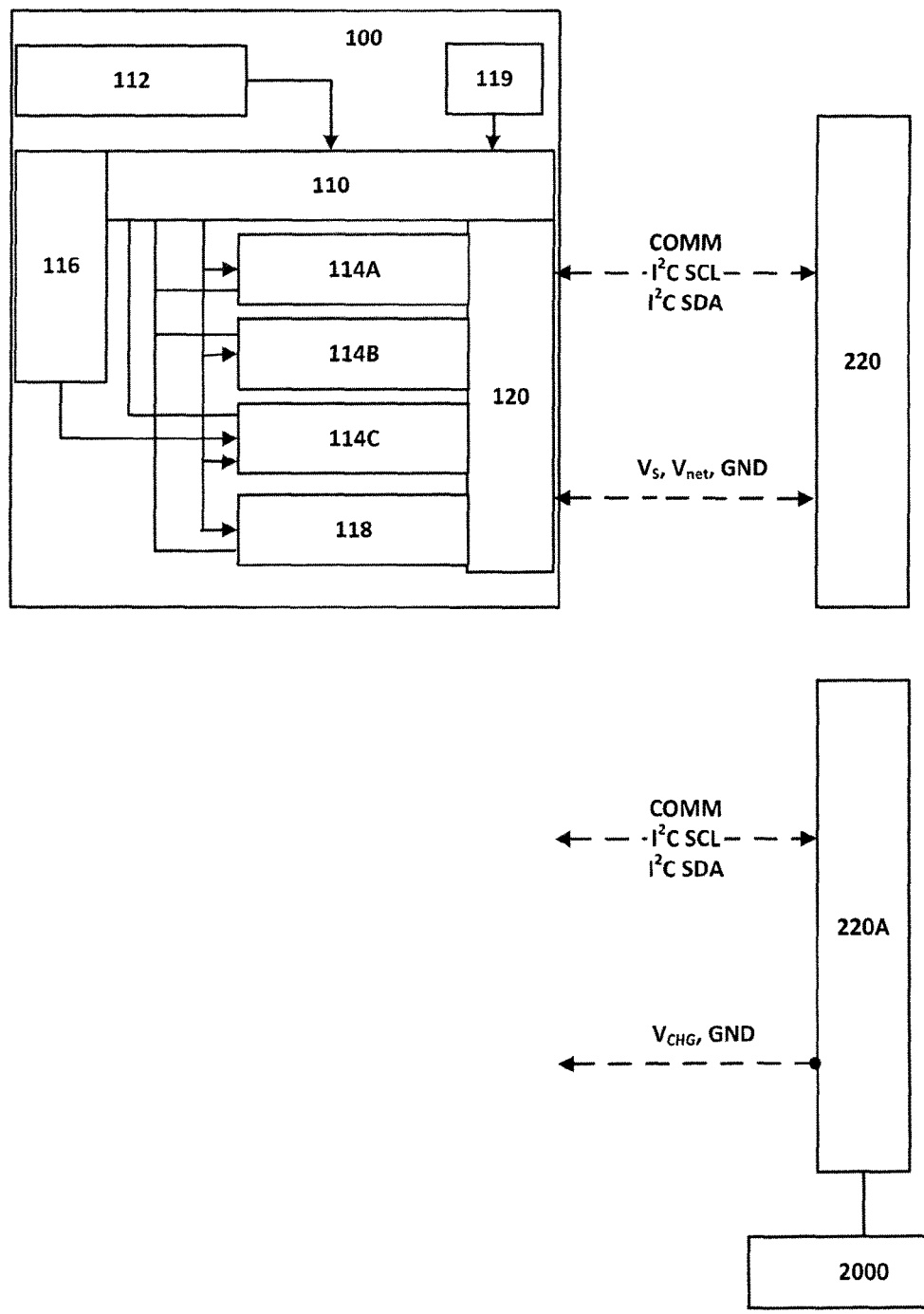
FIG. 2 is a block diagram better illustrating components of a main control module, according to an embodiment.

FIG. 2 is a block diagram better illustrating components of the main control module 100, which are all housed in a single, preferably water-tight or water-resistant enclosure, according to this embodiment. In this embodiment, microprocessor 110 is a highly-integrated Kinetis ARM-based microcontroller package available from Freescale Semiconductor of Austin, Tex., U.S.A. having onboard computer-readable flash system memory and non-volatile data memory, in this embodiment SRAM (Static Random Access Memory) and NVRAM (Non Volatile Random Access Memory). Stored in the memory devices are temporary data, along with processor-readable instructions, baseline protocols and temporary protocols for operating the photoarray system 10, along with measurement and reading data from lixels 300 as will be described. Processor-readable data embodying a lixel illumination pattern in the form of tables of electrical current values or similar data may also be stored on main control module 100. Other types of microprocessors could be used. Current control, rather than voltage control, is implemented because radiation output of the radiation sources is linear with respect to current running through the radiation sources. Microprocessor 110 is in data communications with other components of the main control module 100, including RF transceiver 112, human-machine interface 116, power section 114 having a fixed voltage regulator 114a, a variable $V_{net}$ voltage regulator 114b and a battery charger/Coulomb Counter 114c, rechargeable battery 118, and the first power/data interface 120. Rechargeable battery 118 is in power communications with battery charger/Coulomb counter 114c.

A sensor module 119 for the main control module 100 houses one or more of: an ambient temperature sensor, a motion sensor, a humidity sensor, a physical orientation sensor, an acceleration sensor, an ambient light sensor, a magnetic field sensor, a proximity sensor, an audio level sensor, a video imaging device, an imaging device, one or more colour sensors, or another sensor useful for providing operating and environment data.

First interface 120 of main control module 100 is also connectable to an AC (alternating current) adaptor 2000 via an interface 220A that cooperates with first interface 120 in a similar or the same manner to interface 220, and directs incoming power $V_{CHG}$ from the AC adaptor 2000 to the battery charger/Coulomb counter 114c for charging the rechargeable battery 118. Interface 220A can be configured such that $V_{CHG}$ can be connected to the $V_{net}$ pin, or to some other pin.

Figure 3:
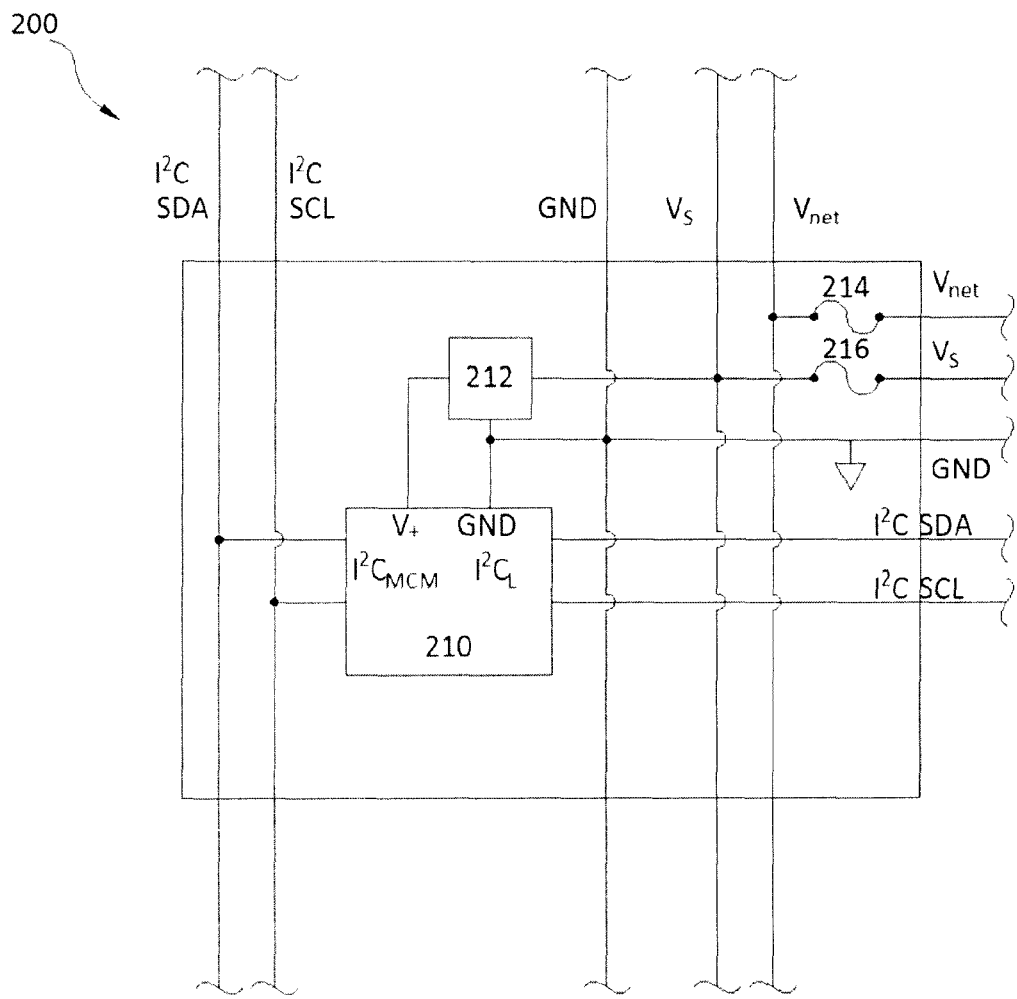
FIG. 3 is a schematic diagram better illustrating components of a commlink, according to an embodiment.

FIG. 3 is a schematic diagram better illustrating components of a commlink 200, according to this embodiment. Commlink 200 receives power along respective electrical lines $V_s$, $V_{net}$ and GND via its connection to main control module 100. Furthermore, commlink 200 communicates with main control module 100 via a communication Port $I^2C_{MCM}$ along respective I²C serial clock (I²C SCL) and serial data (I²C SDA) lines. Each of commlinks 200_1 to 200_x is individually addressable by main control module 100, and is capable of listening to messages broadcast on the I²C data bus by the main control module 100 or by other commlinks 200.

Each of fixed voltage line $V_s$ and data bus lines $I^2C_{xy}$ is connected to a local microcontroller 210, with fixed voltage line $V_s$ being connected to local microcontroller 210 via a voltage regulator 212. The voltage regulator 212 is used for implementations in which microcontroller 210 has a different operating voltage than that of microprocessor 310. Microcontroller 210 also includes a separate communication Port $I^2C_L$ to which is connected a second set of data bus lines for each of I²C SCL and I²C SDA for its respective lixels 300. It will be noted that lines extending from each of $V_s$, $V_{net}$ and GND are run as outputs to commlink 200, with the variable voltage line $V_{netf}$ ($V_{net}$ "fused") being run as an output via a fuse 214, and fixed voltage line $V_{sf}$ ($V_s$ "fused") being run as an output via a fuse 216.

Figure 4:
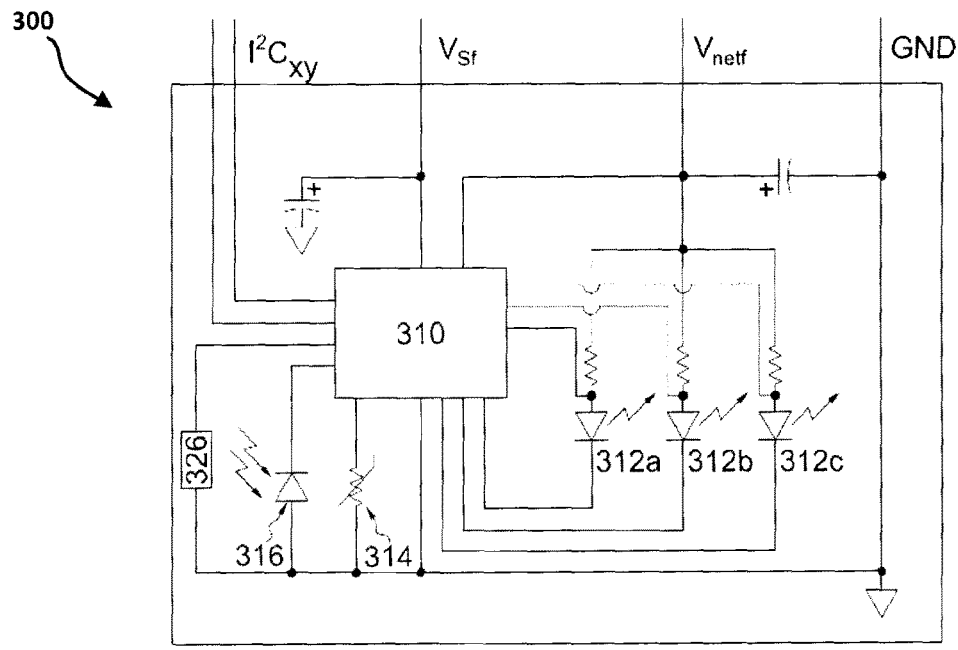
FIG. 4 is a schematic diagram better illustrating components of a lixel, according to an embodiment.

FIG. 4 is a schematic diagram better illustrating components of the lixel 300, according to this embodiment. Lixel 300 receives power along respective electrical lines $V_{sf}$, $V_{netf}$ and GND via lines output from the commlink 200 with which it is respectively in power and data communications. Furthermore, lixel 300 receives data along respective I²C serial clock (I²C SCL) and serial data (I²C SDA) lines, identified in FIG. 4 collectively as I²$C_{xy}$. Each of power line $V_{sf}$ and data bus lines I²$C_{xy}$ are connected to a local microprocessor 310 processing structure having local processor-readable memory. Microprocessor 310 is, in turn connected individually to each of three (3) radiation sources 312a, 312b and 312c.

Microprocessor 310 incorporates multiple internal Field Effect Transistors (FETs) for amplitude control of the current, and a brown-out detector for maintaining reliability in the event of a dip in supply voltage. Microprocessor 310 monitors the voltage and current being provided to radiation sources 312a, 312b and 312c and in addition to accordingly controlling its own levels, can report its local conditions and how it has exercised control to its associated commlink 200. Commlink 200 has an electronic storage structure to locally buffer such data. In this way, the main control module 100 can receive information about how many joules of radiation energy were delivered by each lixel 300, and therefore how many total joules of radiation energy total were delivered to the area being illuminated.

In this embodiment, each of radiation sources 312a, 312b and 312c is a high efficiency Light Emitting Diode (LED). Microprocessor 310 monitors the current running through each of the LEDs 312a, 312b and 312c thereby to make adjustments to the current supply so as to maintain a regulated current and therefore a regulated radiation output.

In this embodiment, radiation source 312a is an LED that outputs radiation having a wavelength of about 455 nanometers (nm) (Δλ 25 nm typical), radiation source 312b is an LED that outputs radiation having a wavelength of about 660 nm (Δλ 25 nm typical), and radiation source 312c is an LED that outputs radiation having a wavelength of about 850 run (Δλ 30 nm typical). The about 455 nm wavelength of radiation is provided with a view to treating bilirubin associated with jaundice and for reducing bacteria contamination in wounds. Furthermore, while visible red having wavelength near to 632 nm has been commonly used from the earliest He—Ne lasers to treat topical wounds and other musculoskeletal conditions, more recently wavelengths between 650 to 670 nm have been commonly used. Manufacturers have been able to create effective strategies in doping semiconductor materials and optical packaging to increase the conversion rate from electrical to optical power.

The about 850 nm wavelength of radiation is provided with a view to achieving deeper penetration into the muscle and circulatory tissues because these are more transparent to the longer wavelength of near-infrared. Wavelengths between 800 and 870 nm approach what is currently considered to be near the optimal window of transmission where red cells and water allow transmission into tissue.

It will be noted that the 455 nm blue wavelength is a higher photonic energy device, and its penetration is low compared to that of the red and near-infrared wavelengths.

Depending upon the instructions sent from main control module 100 via its respective commlink 200, microprocessor 310 of lixel 300 actuates any or all of radiation sources 312a, 312b and 312c. It will be understood that radiation sources 312a, 312b and 312c may require respective, different voltage levels to operate. In this embodiment, the main control module establishes the appropriate voltage level for whichever of radiation sources 312a, 312b and/or 312c by automatically setting the $V_{net}$ voltage level to a level appropriate to the radiation source(s) to be activated during a particular treatment regimen, or phase thereof. Because the main control module 100 controls $V_{net}$ voltage level in concert with its instructions to commlinks 200 as to which radiation source(s) is/are to be actuated, each lixel 300 does not have to include respective voltage divider components for each radiation source. This configuration can provide cost savings, particularly for larger lixel arrays, and can also reduce the amount of heat that would have to otherwise be dissipated through the lixel array B via step-down resistors.

A therapist may program the microprocessor 110 of the main control module 100 to operate radiation sources 312 on fewer than all lixels 300 in the lixel array B. For example, radiation sources 312 on all lixels 300 of a large lixel array B may not be required, for example in implementations where the photoarray is being used in order to provide phototherapy to a relatively small target area on a patient. Due to the individual addressability of the lixels 300 provided by the configurations described herein, individualized activation and de-activation of the radiation sources 312 is possible such that power can be preserved more readily than photoarray systems that do not provide individual addressability.

In this embodiment, actuation of each radiation source on each lixel 300 is controlled by the main control module 100 providing instructions to each of the commlinks 200 to begin a timed sequence of messaging with the individual lixels 300 to actuate one or more of its radiation sources 312 in accordance with a protocol. The radiation sources 312 may be cycled ON and OFF in a predefined manner so as to prevent generating sudden electrical transients which can cause noise in the photoarray system 100 itself due to electromagnetic interference (EMI), or in nearby devices. For example, power to radiation sources 312 can be tailored as a sinusoidal or linear ramped increase to the desired holding level and then decreased similarly back to fully off. The ability to reduce the intensity or rapidly modulate the output is also a mechanism for controlling the temperature by reducing the average ON time of the radiation source 312. Pseudo random modulation, such as is provided by stochastic signal density modulation, an example of which is a technology provided by Cypress Semiconductor known as Precision Illumination Signal Modulation (PrISM), or pulse width modulation (PWM) may be employed to achieve this. As would be understood, an LED driven below 100 milli-Amperes (mA) will not provide reliable or any radiation output. For example, in the event that the equivalent of 50 mA worth of radiation is desired for a particular treatment or treatment phase, the LED is driven at 100 mA but modulated at an averaged 50% duty cycle so as to produce the radiation to compensate for the operating characteristics and produce output as though it were being steadily operated at 100% duty cycle at half of 100 mA (i.e. 50 mA). Above this point the duty cycle can be adjusted until 100% duty cycle is reached at the 100 mA level, and then the actual current level can be increased to produce increases in the radiation output. In general, the relationship between current and radiation output is linear above this point and within a range, such that 200 mA of current will produce twice the light of 100 mA. This is effectively the PRISM technology being used within the PSoC (Programmable System on Chip), which is implemented as a FET current driver of LEDs with programmable tables stored therein.

Such individualized control provided by the photoarray system 10 described herein allows for a balanced or increased thermal conduction rate to the lower ambient temperature at the heat sink side of the lixel which prevents an increase in temperature on the patient side of the device.

In this embodiment, processor-readable data embodying a lixel illumination pattern in the form of tables of electrical power value data, lixel IDs, and other related data are stored on both the main control module 100 and each lixel.

In particular, in this embodiment each lixel's local processor-readable medium on its microcontroller 310 is configured to locally store a portion of the data that specifies the at least one lixel illumination pattern, and microcontroller 310 is configured to receive instructions initiated from the microcontroller 110 and delivered via respective commlinks 200 to cause illumination of the one or more radiation sources in accordance with the instructions and the locally-stored data. In alternative embodiments, the commlinks 200 may be configured to locally store a portion of the data specifying the lixel illumination pattern.

The data structured by the tables may be uploaded to the main control module 100, and may be updated over time to incorporate additional, fewer, or changed lixel illumination patterns. In this embodiment, the processor-readable data is stored in a plurality of related tables, and various lixel illumination patterns that are stored thereon by upload via radiofrequency transceiver 112 can be called upon and activated by a user through interactions via the human-machine interface 116. Other forms of data structures may be employed in alternative embodiments, such as flat or single-table data structures or those that are structured by a relational database management system (RDBMS), providing that in such embodiments the memory, processing power and operating system capabilities of the main control module 100 can support such a system.

In this embodiment, the various lixel illumination patterns are composed of subcomponents which are logically organized into tiers thereby to provide flexibility in their configuration. In this embodiment there are four (4) tiers of subcomponents. The first of these tiers is the Profile tier. There is at least one Profile in the Profile tier, and each Profile in the Profile tier is a set of parameters defining a single lixel's wavelength function of intensity versus time, as in Table 1 below:

TABLE 1

| PROFILE | | |
|---|---|---|
| Parameter Name | Parameter Value | Description |
| Profile ID | Integer | Uniquely identifies the Profile. |
| Wavelength | Red (R); Infrared (IR); Blue (B); Other if available. | The number of wavelengths that are available will depend on which actuatable radiation sources are supported on the lixel. |
| Peak Intensity | 10-100% of device maximum power output for the wavelength. | Specifies the maximum power output. The lixel has hardware supporting 8 bit resolution or better. The increments can be 1% or better. |
| Function | Step, Linear, Slewed, Sine, Logarithmic etc. | Specifies the function of power application for each of the Profiles. X axis is time and y-axis is intensity. The |

TABLE 1-continued

| PROFILE | | |
|---|---|---|
| Parameter Name | Parameter Value | Description |
| | | Profile Function is comprised of a series of discrete steps where time has a resolution of 0.1 milliseconds (ms) and a maximum duration in the Function of 6,553.5 ms, or about 6.5 seconds. |

A unique Profile can be created for multiple Functions for a given Wavelength. For example, there may be a Profile specifying a Slewed (a Step that is rounded near its maximum) Function for the Red Wavelength as well as a different Profile specifying a Sine Function for the Red Wavelength. In this embodiment, this Profile portion of the overall data specifying the lixel illumination pattern is stored locally on each lixel as described above, so that the lixel may receive instructions from a higher tier to activate according to the Profile stored on the lixel at the time. Furthermore, each lixel is configured to conserve power by automatically entering a sleep mode whereby an internal clock triggers wake up during which the lixel checks to determine if there is a command (in this embodiment via commlink 200 from main control module 100) to execute.

The second of the tiers includes the Protocol subtier and the Activity subtier. There is at least one Protocol in the Protocol subtier, and each Protocol in the Protocol subtier is a set of parameters defining a pattern, with the pattern composed of a number of individual Profiles applied to one or more lixels, as in Table 2 below:

TABLE 2

| PROTOCOL | | |
|---|---|---|
| Parameter Name | Parameter Value | Description |
| Protocol ID | Integer | Uniquely identifies the Protocol. |
| Activation Sequence | Multiple Lixel IDs in Sequence | Identifies which lixels are to be active and the order of their activation. |
| Lixel Profiles | Multiple Profile IDs, % integer for each, time in minutes. | Specifies the Profile ID for each of the Active Lixels along with the percentage of the Peak Intensity and fo how long. |
| Timing | Integer: Integer | #Cycles: Max Time (in minutes) |

In this embodiment, this Protocol portion of the overall data specifying the lixel illumination pattern is stored on the main control module 100, as described above. The Protocol determines when to activate the stored Profile on given lixels so as to effect the overall lixel illumination pattern.

Table 2A below shows a number of example Protocols.

TABLE 2A

| PROTOCOL - EXAMPLES | |
|---|---|
| Protocol ID | Parameter Value |
| 1 | 50%-R, 3; 50%-IR, 5; C1: 8 |
| 2 | 50%-B, 3; 50%-R, 1 C1: 4 |
| 3 | 75%-R, 2; 50%-IR, 4; C3: 18 |
| 4 | 100%-R, 1; 0%-R, 1; 100%-IR, 1; 0%-IR, 1; C5: 20 |
| 5 | User configurable via external application program |

In Table 2A, Protocol 1 specifies that the lixels that are deemed Active by the main control module 100 operate Profile for R at 50% of Peak Intensity for 3 minutes, and then operate Profile for IR at 50% of Peak Intensity for 5 minutes. Protocol 1 also specifies that this sequence is operated for only one (1) cycle for a maximum time of 8 minutes.

Similarly, in Table 2A, Protocol 2 specifies that the lixels that are deemed Active by the main control module 100 operate Profile for R at 50% of Peak Intensity for 3 minutes, and then operate Profile for R at 50% of Peak Intensity for 1 minute. Protocol 2 also specifies that this sequence is operated for one (1) cycle for a maximum time of 4 minutes. Protocols 3 and 4 in Table 2A operate according to their Parameter Values in a similar manner as described above. Protocol 5 is user configurable.

In this embodiment, an external, personal computer-based application (not shown) allows a user such as a system configurator or programmer to create many new Protocols which can then be stored and run from the main control module 100. The main control module 100 has a user interface that can be initiated from a wireless linked control interface or a unique combination of button presses through the human-machine interface 116. For example, with a human machine interface having multiple buttons, the fifth protocol can be activated by holding button one (1) on and tapping button two (2) three times. It can be seen that a very simple human machine interface 116 can be used to great effect given the flexibility of the tiered structure. Similarly, holding button two (2) and tapping button (1) can activate a number of different protocols or routines which might include capturing data or running self-diagnostics.

There is at least one Activity in the Activity subtier, and each Activity in the Activity subtier specifies related parameters as shown in Table 3 below.

TABLE 3

ACTIVITY

| Parameter Name | Parameter Value | Description |
| --- | --- | --- |
| Activity ID | Integer | Uniquely Identifies the Activity itself. |
| Duration of Pause | Integer | Specifies a timed pause after running the Protocol |
| Data Collection Request | List of Requests | Specifies which lixel or commlink sensors or other sensors are to be polled for their readings after the timed pause. There are configurations where the array might include no light protocols and only collect sensor readings from the lixel array or a wirelessly linked sensor module. |

The third of the tiers is the Prescription tier. There is at least one Prescription in the Prescription tier, and each Prescription specifies at least one Protocol or Activity and related parameters, as in Table 4 below. A Prescription is employed to run Protocols or Activities over a longer period of time, such as while a horse is being treated while being transported over a period of several days. The horse can receive light therapy spread out over long intervals of hours, and similarly data about the condition of the horse, such as motion analysis, can be regularly collected and reviewed by a trainer when the transporting is finished. For example, the sensor modules having motion sensors can collect data regarding when and whether a horse was jostled violently during transport by the trailer motion, or whether the horse was sitting idly by the road when it should have been taken out for exercise at rest points along the route.

TABLE 4

PRESCRIPTION

| Parameter Name | Parameter Value | Description |
| --- | --- | --- |
| Prescription ID | Integer | Uniquely Identifies the Prescription itself. |
| List | List of Activity IDs | Ordered sequence of between 1 and 20 Protocols or Activity IDs |
| Repeat | Integer | Number of times (From 1 to 15) to repeat triggering of last 15 Activities in List. |

The fourth of the tiers is the Treatment tier. Each Treatment in the Treatment tier is a set of parameters defining one or more Prescriptions and a plan for applying the Prescription to a subject. The treatment tier is also regarded as a recommendation to the user of when to reapply the photoarray on different days over a much longer period of time (such as weeks), as in Table 5 below:

TABLE 5

TREATMENT

| Parameter Name | Parameter Value | Description |
| --- | --- | --- |
| Treatment ID | Integer | Uniquely Identifies the Treatment itself. |
| List | List of Prescription IDs | Ordered sequence of one or more Prescription IDs |
| Application Area | Text | The physical area of the subject on which the photoarray should be applied, for guidance to the user and for ease of organization. Examples: leg, hock, back, hind quarter left, hind quarter right, etc. |
| # Applications | Integer | The number of applications of the Prescriptions per day. |
| # Days | Integer | The number of days to repeat the Applications. |

The above-described tier structure can provide for significant flexibility in deployment and operation of the photoarray system 10 for various therapeutic purposes, and can also enable various levels of abstraction and access rights to the stored data, depending upon the role of the person using or configuring the photoarray at a given time, the feature level, and so forth.

For example, the data in the lower-level tiers (those tiers most closely related to the hardware of each lixel and its individual operation such as the Profile and Protocol tiers), may remain somewhat fixed unless being repaired or upgraded, across all versions of a given photoarray system product. This is provided, generally speaking, that the lixel radiation sources and power delivery thereto is common to the versions; otherwise at least the data in the Profile tier is likely to have different data stored therein. On the other hand, a distributor or similar middleperson who is interested in using a common platform to provide different features in different photoarray system products at different price points or for different types of markets (such as equine versus human), may not be provided with access to change the data in the lowest tiers, but may be provided with access to data in a mid level tier (such as the Activity tier). In such a case, the middleperson might configure a particular class of photoarray system to have fewer or more selectable Activities depending on the intended price point and/or intended subject to be treated. Still further, a therapist may be provided with access to only the Prescription and Treatment tiers so as to program a configuration using only the available Activities so as to be applicable to a particular patient.

Furthermore, it will be understood that some uses of the photoarray system may not require deployment or use of higher-level tiers, in favour of direct manipulation of mid- or lower-level tiers for certain applications. For example, in embodiments a user may be able to directly specify and/or choose a particular Prescription, without having to specify and/or choose a Treatment that lists that Prescription. Similarly, in embodiments a user may be able to directly specify and/or choose a particular Protocol thereby to cause a plurality of specified lixels to operate according to respective associated Profiles, without having to choose an Activity specifying the Protocol, a Prescription specifying the Activity, a Treatment specifying the Prescription, and the Treatment specifying the Prescription, or some sub-combination of the above.

It will be noted that actual storage of the data in tiers as heretofore described does not have to be confined to the depicted structures of the above-described tables. Rather, the above-described tables indicate the nature of the data for a respective tier rather than its exact stored format or nomenclature. For example, the Protocols shown in Table 2A are stored in somewhat flat, semi-colon delineated sequences rather than in separate database table records.

Also connected to microprocessor 310 of lixel 300 is a temperature sensor, in this embodiment a thermistor 314, and a photo sensor, in this embodiment a photodiode 316. Thermistor 314 provides microprocessor 310 with a reading of the ambient temperature level local to the lixel 300. Similarly, photodiode 316 provides microprocessor 310 with a reading of the ambient radiation intensity level local to the lixel 300. One or more additional sensors 326 may be provided in order to sense ambient motion, humidity, physical orientation, acceleration, magnetic field, proximity, audio level, video, images, one or more colours, or other ambient physical quantities for providing operating and environment data. The provision of such sensors in association with each or some lixels 300 enables the sensors to be distributed amongst the radiation sources. In this embodiment, as each lixel 300 includes sensors, the sensors are distributed generally uniformly amongst the lixels 300. Other configurations for distributing sensors generally uniformly amongst the radiation sources, such as for example by providing only every second lixel 300 with one or more such sensors, or for providing one type of sensor on one lixel 300 and another type of sensor on the next lixel 300, and so forth, are possible. Other configurations including non-uniform distribution of sensors amongst the radiation sources 300 may be employed in particular implementations.

Because sensors 314, 316 and 326 are local to lixel 300, microprocessor 310 is able to communicate local temperature and radiation intensity readings to a respective commlink 200 when polled by the commlink 200 to collect and store the readings for each of the subset of the plurality of lixels 300 with which it is associated. Such polling may be initiated by the main control module 100, so as to collect local readings for restructuring and/or buffering at respective commlinks 200 for subsequent provision to main control module 100 and to, in turn, modify actuation of any or all radiation sources 312 of any or all lixels 300 in the lixel array B should local radiation intensity be too high or too low, or should local temperature be too high, for example. In this manner, high-resolution temperature and intensity feedback is available to the main control module 100 so that it may, in turn, modify the sequencing and/or provide granular control over the operation of each individual radiation source 312 in order to provide heat management and to accurately determine the amount of radiation actually being delivered to a patient. More particularly, it is preferred that maximum temperature at the patient skin at a particular location in the lixel array B be 45° C. or lower. Furthermore, such local readings collected in this way, along with any automatic modifications in operation by lixel 300 or main control module 100 may be stored and/or compressed and/or made available in raw or pre-processed form to a therapist or other user via the human-machine interface 116, or output via RF transceiver 112 to external computing device 1000 for further processing or data collection.

The multiple-tier structure provided by main control module 100, commlinks 200 and lixels 300 further facilitate efficient field-upgrades of the firmware on lixels 300. The main control module 100 can update the firmware on a commlink 200 and then instruct the commlink 200 to, in turn, handle upgrading the firmware on its respective lixels 300. In particular, the main control module 100 does not have to remain occupied updating firmware on individual lixels 300 as it has delegated this task to its commlinks 200.

Figure 5:
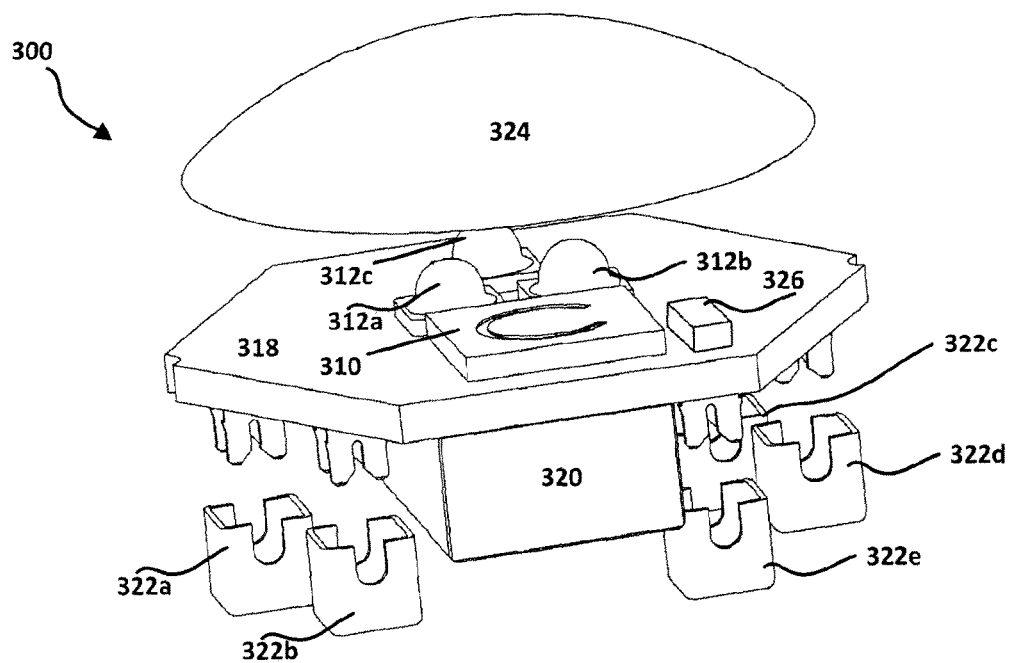
FIG. 5 is an isometric view of components of a lixel in exploded view.

Turning now to FIG. 5, there is shown an isometric view of components of a lixel 300 in exploded view. A platform 318, in this embodiment a hexagonal-shaped printed circuit board, supports and interconnects on a patient-facing side of the lixel 300 surface-mount LEDs 312a, 312b and 312c, the microprocessor 310, and other components such as photodiode 316, thermistor 314 (which are not shown in FIG. 5), and other sensor 326. A radiation diffuser 324, which in this embodiment is a translucent plastic dome, is affixed over top of at least the radiation sources 312 in order to provide diffusion of the radiation being emitted over a wider area thereby to enable wider coverage on the patient. On the side of the platform 318 opposite the patient-facing side are five (5) insulation displacement connectors (IDCs) 322a to 322e for providing connectivity, without line termination, to the five (5) power and data lines $V_{sf}$, $V_{netf}$, GND, I²C SCL and I²C SDA, respectively. Due to the use of IDCs, spacing of lixels 300 and overall length and shape of lixel array B can be established and/or specified during assembly without drastic modifications to tooling. In particular, lixel arrays B with different sizes and spacing can be easily established by simply establishing the length of the five (5) power and data lines $V_{sf}$, $V_{netf}$, GND, I²C SCL and I²C SDA and affixing the lixels 300 with the IDCs accordingly.

A heat transfer structure, in this embodiment a heat sink 320, also extends from the side of the platform 318 opposite the patient-facing side for drawing heat away the patient-facing side of the platform 318.

Figure 6:
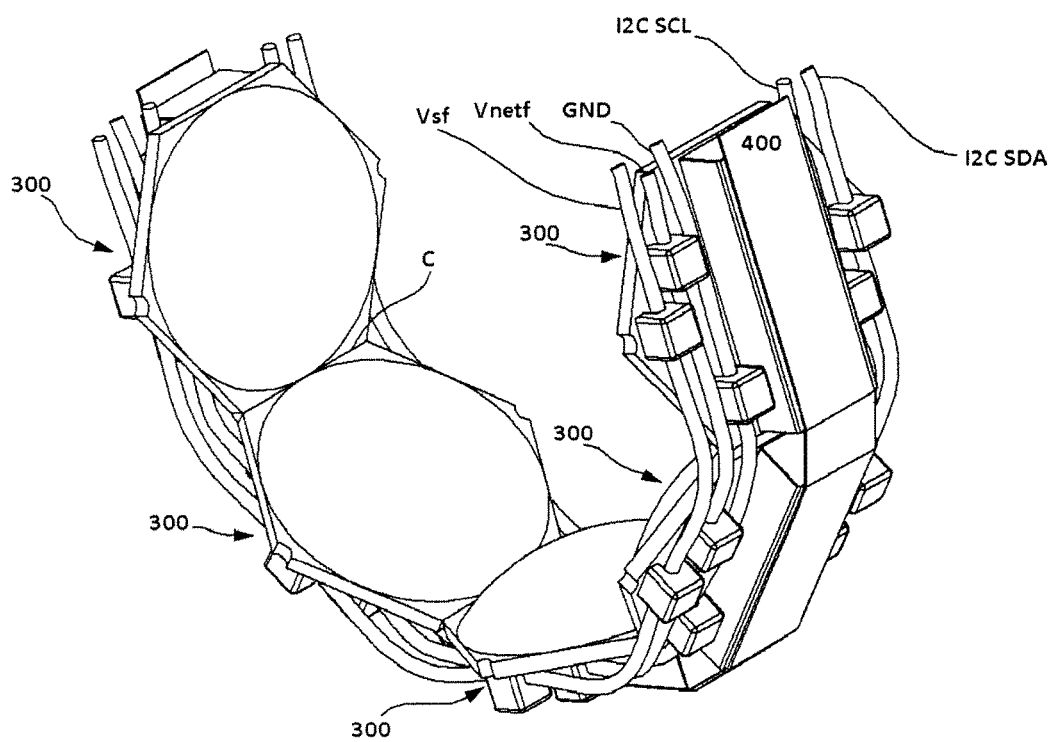
FIG. 6 is an isometric view of the top of a portion of a series of flexibly interconnected lixels curved inwardly.
Figure 7:
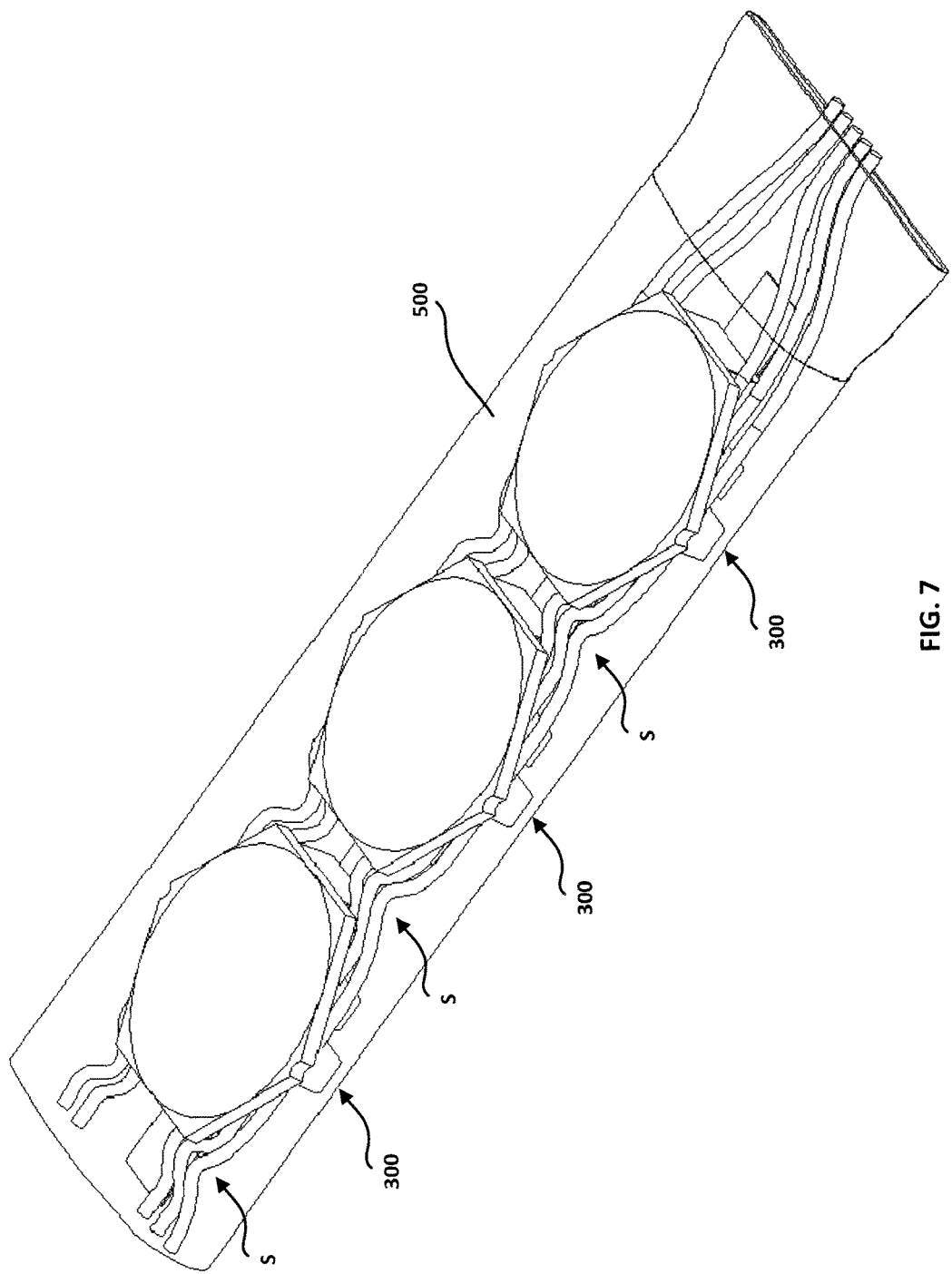
FIG. 7 is an isometric view of the top of a portion of a series of flexibly interconnected lixels encased in flexible transparent housing.
Figure 8:
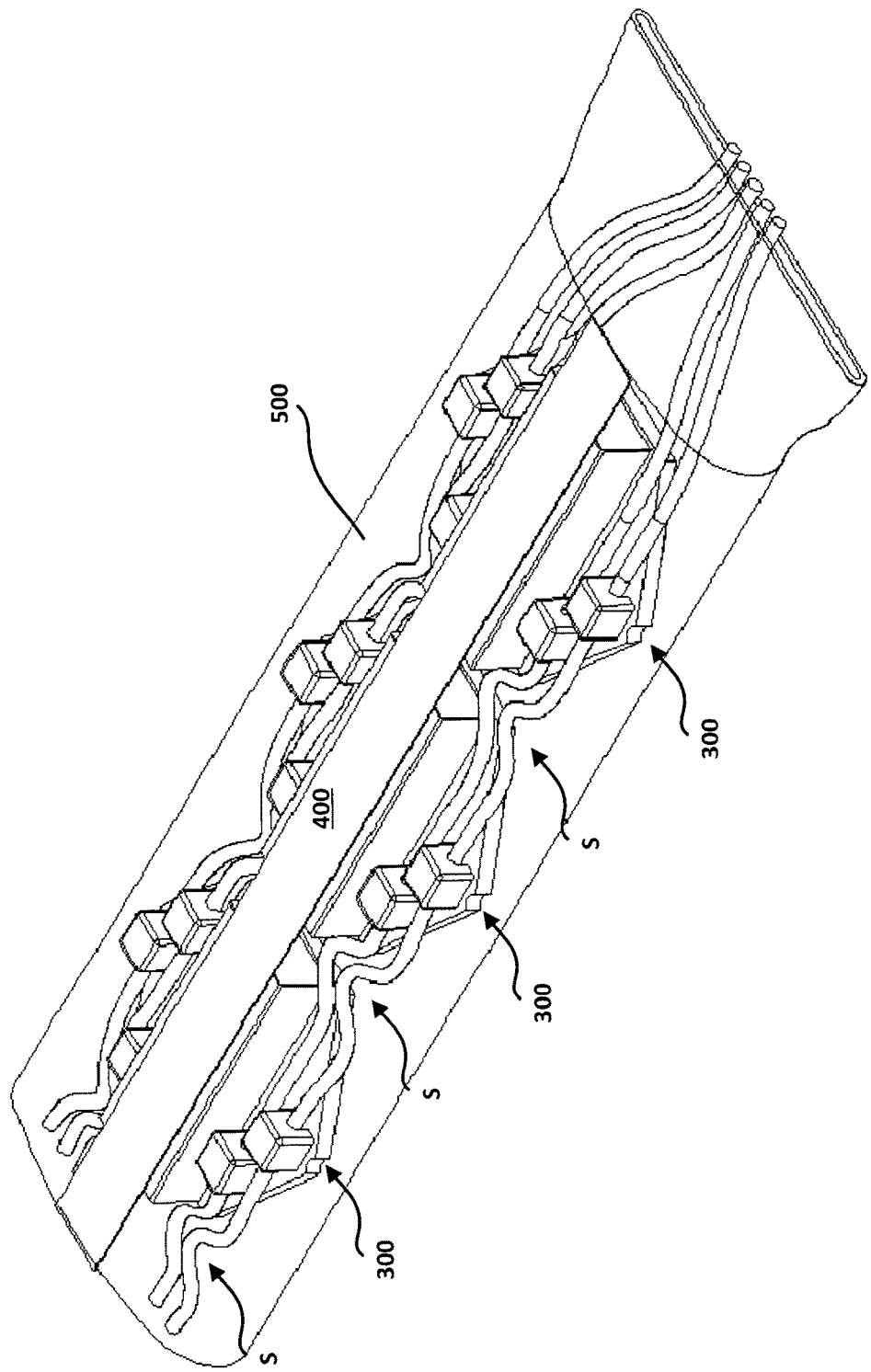
FIG. 8 is an isometric view of the bottom of the portion of the series of flexibly interconnected lixels of FIG. 7.

FIG. 6 is an isometric view of the top of a portion of a series of flexibly interconnected lixels 300. As can be seen, the lixels 300 in this series have been concavely flexed with respect to each other such that the facing edges of platforms 318 of adjacent lixels 300, which are spaced from each other when the series is not flexed, come into contact with each other at a contact point C, thereby to limit further flexing in a concave manner. The flexing is provided in order to enable the lixel array to be wrapped around or otherwise conformed to a subject's body, and the limiting provided by the physical configuration and positioning of platform 318 and other physically interacting components reduces the potential for undue stress on the power and data lines, the IDCs, and other components. This concave flexing is enabled by the flexible insulated wires for each of the five (5) power and data lines $V_{sf}$, $V_{netf}$, GND, I²C SCL and I²C SDA each having a small amount of slack at slack regions S, as can be seen in FIGS. 7 and 8. The concave flexing is further limited by a fabric, non-woven material, flexible metal band or other thermally conductive material of sufficient strength as a control strip 400 that is affixed to the heat sinks 320 and that extends the length of the subset of lixels 300 in a given strip. The hexagonal shape of the printed circuit boards provides compact nesting of lixels 300 in rows and columns in combination with the ability to physically move with respect to each other in multiple directions (for example not just concavely and, to a lesser degree, convexly along strips of lixels 300 sharing the same data and power lines, but concavely and convexly across strips with respect to adjacent lixels 300, ie. laterally and/or longitudinally). This enables conforming the overall lixel array B to the region of the patient being treated with a view to providing uniform emissions of radiation towards the area to be treated.

In an alternative embodiment, an additional control strip is provided and configured with respect to the lixels 300 to limit the degree of convex movement that is permitted, so as to limit the stress placed upon power and data lines, the IDCs and other components that may otherwise occur if the power and data lines are permitted to easily become taut during convex flexing.

FIG. 7 is an isometric view of the top of a portion of a series of flexibly interconnected lixels 300 encased in flexible transparent housing 500. In this embodiment, flexible transparent housing 500 is a length of flexible plastic tubing that can be cut from a roll to a particular desired length to completely enclose and protect the lixel array B, and sealed to inhibit the ingress of water or other contaminants. FIG. 8 is an isometric view of the bottom of the portion of the series of flexibly interconnected lixels of FIG. 7.

Although embodiments have been described with reference to the drawings, those of skill in the art will appreciate that variations and modifications may be made without departing from the spirit and scope thereof as defined by the appended claims.

For example, other local conditions beyond temperature and radiation intensity can be measured by sensors associated with a given lixel, such as current, voltage, orientation, acceleration, gyroscopic, ambient light, magnetic field, proximity, audio level, video image and colour.

Furthermore, while a photoarray system has been described herein that includes a main control module 100, a plurality of commlinks 200 and a plurality of lixels 300, other configurations are possible. For example, the three-level hierarchy could be reduced to two levels (i.e., main control module 100 and respective lixels 300), provided that semiconductors are employed that can reliably communicate over a short range (0.1 to 3 meters) communication channel at high speed (125 kbit to 12 Mb or faster).

Furthermore, while embodiments have been described in which each lixel 300 controls the power directly to the local radiation sources 312a, 312b and 312c, embodiments are contemplated in which an alternative lixel structure having a microprocessor 310 is capable of controlling one or more adjacent lixels that may not have a respective microprocessor.

While embodiments have been described in which the lixels 300 have three radiation sources that are LEDs, embodiments are contemplated in which lixels have fewer or more radiation sources, emit different wavelengths of light than those that have been described by way of example herein (such as ultraviolet radiation, violet radiation, other visible or infrared radiation) and those in which the radiation sources are other or various types of radiation sources such as solid state laser diodes, OLEDs (Organic Light Emitting Diodes), or FIPEL (Field-induced polymer electroluminescent) radiation sources, with corresponding respective operating characteristics and supporting circuitry, for example.

Furthermore, while in embodiments described an aluminum block heat sink 320 has been shown as part of lixel 300, other configurations are contemplated. For example, due to the open-backed nature of the lixel 300, where lines for $V_{sf}$, $V_{netf}$, GND, I²C SCL and I²C SDA run along the sides of the underside of the platform 318 rather than across the middle of platform 318, adequate heat dispersion may be provided without a heat sink.

Furthermore, other embodiments of heat sink may employ a rectangular block or a block with a cutaway portion having a rectangular, oval or circular cross-section for receiving a heat conveyance structure such as a rigid or flexible heat pipe that can convey heat away from several lixels 300 in a row. Flexible phase change material or materials may be employed to assist with drawing heat away from the patient-facing side of the lixel 300. Additional or auxiliary cooling systems may be provided.

Furthermore, while platform 318 has been described as a hexagonal-shaped printed circuit board, other shapes such as square, circular or irregular-shaped platforms may be employed.

While microprocessors 110, 210 and 310 operating at 5V are employed in the embodiments described above, alternatives are possible. For example, microprocessors that operate at 3.3V or lower could be employed.

Furthermore, while embodiments have been described in which each lixel incorporates a temperature sensor and a radiation sensor, variations are possible. For example, every other or third lixel could be provided with one or both such sensors. It will be understood however that local temperature and radiation intensity can vary widely across short distances due to the physical attributes of the patient, clothing, adjacency, and effectiveness of local heat sinking.

Furthermore, while the main control module in embodiments described above provides data communications along a two-line I²C serial data bus, an alternative data communications scheme may be employed, such as LINbus (Local Interconnect Network bus), 1-Wire or some other widely available or proprietary bus technology.

Furthermore, an alternative embodiment of a lixel array B could incorporate a wireless communication link for very short range and a wireless power transfer scheme such as WiTricity or Qi to accomplish the same individual control of each lixel without the hardwired links for even greater flexibility limited only by the typical range of the wireless power transfer.

Furthermore, an alternative embodiment of a lixel array B could include sensors 326 dispersed at relevant locations throughout the lixel array B. For example, for wound monitoring, a photoarray system for use in phototherapy could be provided with colour sensors distributed throughout the lixel array B in such a way as to have colour sensing both peripherally and centrally with respect to a wound being treated. Emission of radiation from particular radiation sources 312 could be used to cause the wound area to, in turn, emit radiation depending upon its healing state, such that the data collected by the colour sensors could show rate and progress of the healing.

What is claimed is:

1. A photoarray system comprising:
   a lixel array comprising a plurality of lixels each supporting one or more radiation sources;
   a power source associated with the lixel array; and a control system associated with the power source and each of the radiation sources, the control system comprising:
    a master processor-readable medium configured to store at least a portion of data that specifies at least one lixel illumination pattern; and
    a master processing structure configured to regulate use of power individually by each of the radiation sources based on the at least one lixel illumination pattern to mitigate electromagnetic interference between two or more of the plurality of lixel, and to vary power consumed by at least one of the radiation sources in a continuous time-varying waveform using the master processing structure, wherein the continuous time-varying waveform comprises:
a sinusoidally varying waveform; a linear ramped increase to a holding level and a linear ramped decrease to a fully off level; or a slewed step waveform having one or more steps that are rounded near their maximum amplitude.

2. The photoarray system of claim 1, wherein the continuous time-varying waveform comprises a sinusoidally varying waveform.

3. The photoarray system of claim 1, wherein the continuous time-varying waveform comprises a linear ramped increase to a holding level and a linear ramped decrease to a fully off level.

4. The photoarray system of claim 1, wherein the continuous time-varying waveform comprises a slewed step waveform having one or more steps that are rounded near their maximum amplitude.

5. The photoarray system of claim 1, wherein the plurality of the lixels each comprise:
    a local processor-readable medium configured to locally store a portion of the data that specifies the at least one lixel illumination pattern; and
    a local processing structure configured to receive instructions from the master processing structure and to cause illumination of the one or more radiation sources in accordance with the instructions and the locally stored data.

6. The photoarray system of claim 5, wherein the master processor-readable medium is configured to store at least a portion of the data defining the at least one lixel illumination pattern in a plurality of data structures.

7. The photoarray system of claim 6, wherein the plurality of data structures are arranged in logical tiers.

8. The photoarray system of claim 6, wherein the data structures are configured to store data specifying parameters for at least one sequence of activation of the lixels.

9. The photoarray system of claim 6, wherein each lixel supports two or more radiation sources.

10. The photoarray system of claim 9, wherein the data defining the at least one lixel illumination pattern comprises which of the two or more radiation sources are to be activated.

11. The photoarray system of claim 10, wherein the portion of the data defining the at least one lixel illumination pattern stored on the local processor-readable media comprises data specifying the amount of power to be delivered to the radiation sources.

12. The photoarray system of claim 5, wherein the local processor-readable media are configured to store data specifying parameters for peak intensity of each of the one or more radiation sources.

13. The photoarray system of claim 5, wherein each local processing structure is further configured to:
    at a first step, detect whether an instruction has been received from the master processing structure; and
    at a second step, if no instruction has been received:
        induce a power-conserving sleep mode in the lixel for a predetermined period of time; and
        after the predetermined period of time has elapsed, return to the first step.

14. The photoarray system of claim 1, further comprising:
    a sensor array comprising a plurality of sensor modules distributed amongst the plurality of radiation sources, each of the sensor modules configured to communicate respective local readings to the control system.

15. The photoarray system of claim 14, wherein the control system is configured to regulate provision of power individually to each of the radiation sources based also on the local readings.

16. The photoarray system of claim 14, wherein each sensor module comprises at least one sensor for taking the local readings.

17. The photoarray system of claim 16, wherein one of the at least one sensor is a temperature sensor.

18. The photoarray system of claim 14, wherein the master processor-readable medium is configured to store data defining when the at least one sensor module is to communicate its respective readings.

* * * * *